United States Patent
Engeberg et al.

(10) Patent No.: US 8,588,977 B2
(45) Date of Patent: Nov. 19, 2013

(54) SIGNAL MODULATOR FOR VISUAL INDICATOR

(75) Inventors: Erik Daniel Engeberg, Akron, OH (US); Sanford G. Meek, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1000 days.

(21) Appl. No.: 12/622,697

(22) Filed: Nov. 20, 2009

(65) Prior Publication Data

US 2010/0131101 A1 May 27, 2010

Related U.S. Application Data

(60) Provisional application No. 61/116,449, filed on Nov. 20, 2008.

(51) Int. Cl.
*B25J 13/02* (2006.01)
*B25J 11/00* (2006.01)
*B25J 9/16* (2006.01)
*A61F 2/54* (2006.01)
*A61F 2/56* (2006.01)
*A61F 2/50* (2006.01)

(52) U.S. Cl.
USPC ............. 700/258; 700/245; 700/264; 901/2; 901/33; 901/46; 901/50

(58) Field of Classification Search
USPC .................. 700/245–264; 901/1–50
See application file for complete search history.

(56) References Cited

U.S. PATENT DOCUMENTS

| 4,650,492 | A | * | 3/1987 | Barkhordar et al. ............ 623/24 |
| 4,990,815 | A | * | 2/1991 | Lindner et al. ........... 310/316.01 |
| 5,648,617 | A | * | 7/1997 | Cullen et al. ............. 73/862.045 |
| 6,016,385 | A | * | 1/2000 | Yee et al. ........................ 700/245 |
| 2003/0040758 | A1 | | 2/2003 | Wang et al. |
| 2007/0227267 | A1 | * | 10/2007 | Loeb et al. ............... 73/862.046 |
| 2008/0114491 | A1 | * | 5/2008 | Takahashi ..................... 700/245 |
| 2009/0018670 | A1 | * | 1/2009 | Puchhammer ................... 623/64 |
| 2009/0076657 | A1 | * | 3/2009 | Tsuboi et al. ................. 700/275 |
| 2010/0168919 | A1 | * | 7/2010 | Okamoto ....................... 700/275 |

(Continued)

FOREIGN PATENT DOCUMENTS

WO WO 2007094529 A1 * 8/2007
WO WO 2007111252 A1 * 10/2007 ................. B25J 9/16

OTHER PUBLICATIONS

Engeberg et al. "Adaptive object slip prevention for prosthetic hands through proportional-derivative shear force feedback", IEEE/RSJ 2008 International Conference on Intelligent Robots and Systems. Sep. 22-26, 2008 Nice, France.

(Continued)

*Primary Examiner* — Khoi Tran
*Assistant Examiner* — Dale Moyer
(74) *Attorney, Agent, or Firm* — Thorpe North & Western LLP (57) ABSTRACT

An apparatus in an example comprises a manipulator, a force sensor, a signal modulator, and a visual indicator. The manipulator is employed by a user. The force sensor determines a force signal from a force applied by the manipulator on a part of an environment of the user. The signal modulator is adjustable by the user to select a switch point for the visual indicator based on relative fragility of the part of the environment. The signal modulator employs the force signal and the switch point to control the visual indicator for the user.

25 Claims, 9 Drawing Sheets

(56) References Cited

U.S. PATENT DOCUMENTS

2011/0067504 A1* 3/2011 Koyama et al. .......... 73/862.381

OTHER PUBLICATIONS

Engeberg et al., "Model-based feed forward derivative compensation for prosthetic hands", $2^{nd}$ Biennial IEEE/RAS-EMBS International Conference on Biomedical Robotics and Biomechatronics, Scottsdale, Arizona, Oct. 19-22, 2008, pp. 61-65.

Engeberg et al., "Backstepping and sliding mode control hybridized for a prosthetic hand", IEEE Trans Neural Syst Rehabil Eng. Feb. 2009; 17(1):70-9 Abstract.

2008 IEEE International Conferecne on Robotics and Biomimetics Technical Program, Feb. 22-25, 2009, Bangkok, Thailand, pp. 1-16.

* cited by examiner

SIGNAL MODULATOR FOR VISUAL INDICATOR

STATEMENT OF GOVERNMENT RIGHTS

This invention was made with government support under BES0457193 awarded by National Science Foundation. The Government has certain rights to this invention.

BACKGROUND

Powered upper limb prostheses have been beneficial to amputees, but still have several problems that limit their performance. Sometimes objects grasped by prosthetic hands slip free and fall. A design has incorporated an embedded sensor into the thumb of a sensor hand to help prevent unintentional slip of grasped objects. Also, a number of prosthetic hands have only one degree of freedom. They can only close or open in a simple pinch-grasp operation. Multiple degree of freedom (DOF) underactuated prosthetic hands are under development. A commercially available prosthetic hand has five independently actuated digits. A number of powered prostheses are controlled by electromyogram (EMG) signals, which may make it difficult to dexterously control a multiple DOF prosthetic hand. Dexterous control of a multiple DOF hand may become more difficult if done while simultaneously controlling a prosthetic arm.

DETAILED DESCRIPTION

Features of exemplary implementations of the invention will become apparent from the description, the claims, and the drawings. Referring to the BACKGROUND section above, Amputees who use powered prosthetic hands may lack feedback to the user about the state of the hand. When grasping a rigid or brittle object, it may be difficult to visually ascertain the amplitude of applied grip force because rigid objects undergo imperceptible deflections from typical grip forces. This means that there is often little warning before a brittle object is accidentally broken or dropped. Because a natural sense of contact force is desirable, supplemental grasp force feedback can improve force control even when the user has clear sight of the manipulated object. Techniques have been employed to reconnect a sense of contact force to amputees. Direct neural feedback of grip force from a prosthetic hand has been demonstrated with amputees. A proportional force feedback system was developed that applies a force to the skin of the amputee in proportion to the magnitude of the applied grip force by the prosthesis. Electrical stimulation of the skin has been used to indicate a change in applied grip force through a change in frequency of electrical pulses. Vibrotactile feedback has been supplied to amputees whereby the applied grip force is conveyed to the user through a change in vibration frequency. Vibrotactile feedback for extended periods of time can be disturbing. Electrical stimulation of the skin can be painful or unpleasant if the current amplitude is slightly too large. Direct neural feedback may be impractical for clinical implementation over long periods of time, for example, problems upper limb prostheses.

An exemplary implementation provides enhanced visual feedback for nonlinear sliding mode control of a prosthetic hand. A desirably economic and practical method of supplying force feedback to operators of a prosthetic hand is disclosed. Force feedback may be used in the control algorithm for the prosthetic hand and supplied visually to the user through a bicolor LED experimentally mounted to the thumb. Several experiments have been performed that rate the usefulness of the additional visual feedback when manipulating a clearly visible, rigid and brittle object. A hybrid force-velocity sliding mode controller may be used with and without additional visual feedback supplied to the operators. Subjective evaluations and success rates from the test subjects have indicated that extra visual feedback may be desirable. An exemplary implementation may be inexpensive, require little power, and be self-contained within a prosthetic hand.

Motion Control Hand (Motion Control, Inc. Salt Lake City, Utah) has been used for experiments to demonstrate efficacy of additional visual feedback. Force feedback may be used in a number of ways. For example, the magnitude of the applied grip force may be mapped to light intensity from a LED. This may permit the user to know how tightly a rigid object is being gripped by observing the intensity of the light from a LED experimentally mounted onto the thumb of the prosthesis.

In addition to force feedback visually supplied to the user, force feedback may be used in the control algorithm of the hand as well. The hybrid force-velocity sliding mode controller developed may be used to provide improved control of velocity and force of the prosthetic hand through a single control input. Force derivative feedback may be used in the control algorithm, for example, to increase the grip force sensitivity of prosthetic hands. Force derivative feedback helps smooth the transition from velocity to force control when initially grasping objects.

An exemplary implementation employs visual force feedback that is inexpensive, has no moving parts, and needs only simple circuitry which in an example could be easily contained entirely within a prosthetic hand. The LED may be integrated into a cosmetic glove and the prosthesis may have a built-in switch to turn the LED off whenever desired. An exemplary implementation employs an inexpensive and low power approach of visually supplying force feedback for prosthetic hands.

Figure 1:
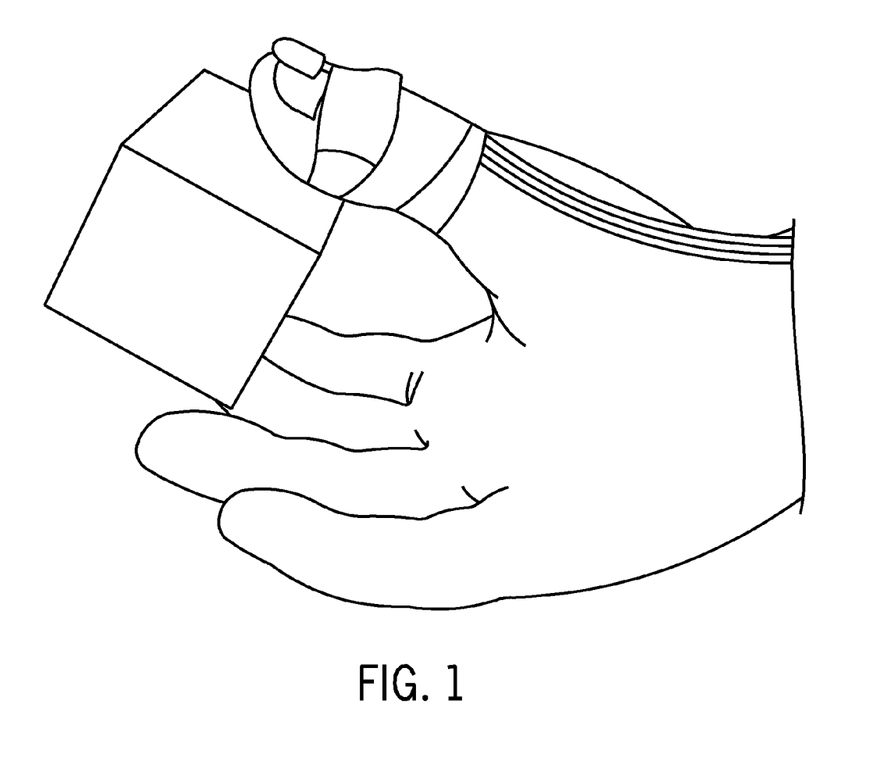
FIG. 1 is a representation of an implementation of a Motion Control Hand that comprises a red-green bicolor LED mounted to the thumb.

Turning to FIG. 1, an example presented of a Motion Control Hand comprises a red-green bicolor LED, for example, mounted to the thumb. The Motion Control Hand in an example comprises one degree of freedom. The fingers are linked to the thumb through a four bar mechanism so that the hand can simply open or close. The Motion Control Hand has been experimentally outfitted with an A1321 (Allegro Micro-Systems, Inc. Worcester, Mass.) Hall effect position sensor and six strain gages mounted on the thumb. The position sensor indicates the distance between the thumb and forefingers and the strain gages are used to convey the normal and shear forces.

In an example, a simple second order system model, obtained through a summation of torques acting on the motor, may be used to describe the dynamics of the prosthetic hand:

$$\dot{x}_1 = x_2 \quad (1)$$

$$\dot{x}_2 = m(x_1, x_2) + nE \quad (2)$$

where $x_1$ is the distance between the thumb and fingers and $x_2$ is the velocity of the hand. E is the voltage input to the motor and n is a value dependent upon the motor's resistance, torque constant, and effective inertia. The $m(x_1, x_2)$ term accounts for the inertia (J), damping (B), and stiffness (K) of the system in addition to the nonlinear Coulomb friction (F) produced by the large gear ratios:

$$m(x_1, x_2) = \frac{-B}{J}x_2 - \frac{K}{J}x_1 - \frac{F}{J}\text{sgn}(x_2) + \quad (3)$$

The sgn function is defined to be one, zero, or negative one if its argument is positive, zero, or negative, respectively. D is used to describe unknown externally applied disturbance forces and the nonlinear torque transmission through the four bar linkage mechanism.

The dominant terms in the system model can change frequently during normal operation of the prosthesis. Before contact is made with the grasped object, the stiffness of the system in an example may be nearly negligible. But after contact is made with the environment, the $m(x_1, x_2)$ term may change in an unpredictable way because the effective stiffness of the system may change greatly, for example, depending upon the stiffness of the grasped object. The inertia and damping of the system also may change in an unforeseeable manner, for example, depending upon the size, mass, density, shape, and compliance of the grasped object.

Figure 2:
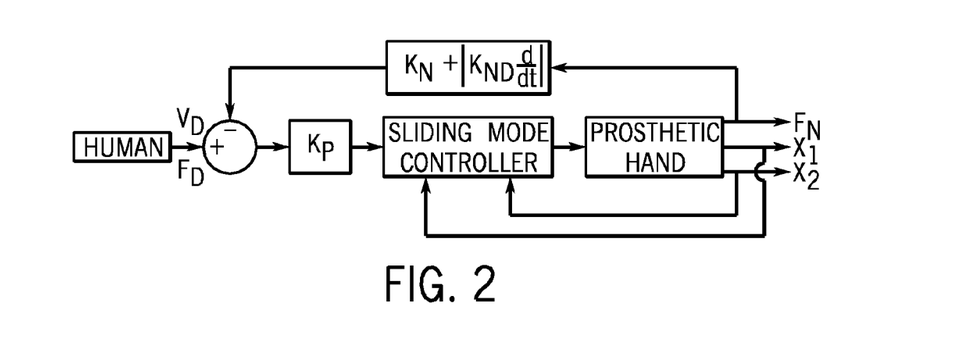
FIG. 2 is a representation of an implementation of a hybrid force-velocity sliding mode controller with force, force derivative, position, and velocity feedback.

Turning to FIG. 2, an example is presented of a hybrid force-velocity sliding mode controller with force, force derivative, position, and velocity feedback. $F_D$ is the desired force, $v_D$ is the desired velocity, $F_N$ is the measured normal force, $x_1$ is the position, and $x_2$ is the velocity. The K terms are constant gains. Sliding mode control may serve to overcome nonlinear forces in control of a number of different systems. Nonlinear sliding mode control may be stable for a broad class of systems. Sliding mode control of the prosthetic hand may be incorporated into a hybrid force-velocity control scheme, for example, so that the user has improved control of the velocity or force of the prosthesis through a single input. The sliding mode controller may fully saturate the motor of the prosthesis positively or negatively, for example, while there is an error present in the desired force or velocity. The switching of the motor voltage in an example is dependent on the force, position, and velocity of the system. The sliding mode controller may serve to minimize error in force and to smooth the control of velocity.

Sliding mode control may be realized through an input of the form $$E = -C\,\text{sgn}(s), \quad (4)$$

where s, the sliding manifold, is a function of force and position error. C is a value based on an upper-bound estimate on the torques and disturbances acting against the motor of the prosthetic hand. The sliding mode controller in an example employs the saturation function in place of the sgn function, for example, to partially linearize the control law and prevent unwanted chatter of the hand.

Figure 16:
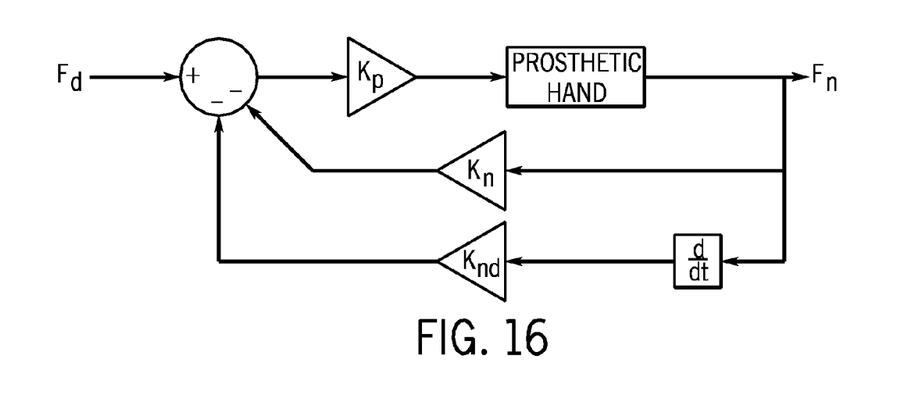
FIG. 16 is a representation of an implementation of a controller in which normal force derivative feedback in an example may be used with or without the absolute value function, where the use of normal force derivative feedback in an example promotes a manipulator for delicate manipulation of any part of the environment of the user.

Force derivative feedback may serve to improve the transition from velocity to force control. Force derivative feedback may also serve to improve the grip force sensitivity of prosthetic hands. Force derivative feedback may serve to lower the mechanical impedance of the closed loop system. This may be useful because prosthetic hands may be rigid, while natural systems may have high or low mechanical impedance. In an example of the controller, the absolute value of force derivative feedback may provide that changes in force derivative in an example can only be used to prevent force overshoot and undesirably large increases in applied grip force. Using the absolute value of force derivative feedback may also be useful to improve the force tracking ability of the prosthesis while decreasing the applied grip force. Referring to FIG. 16, normal force derivative feedback in an example may be used with or without the absolute value function. The use of normal force derivative feedback in an example promotes a manipulator for delicate manipulation of any part of the environment of the user. $K_{nd}$ is the feedback gain for the normal force derivative.

Figure 3:
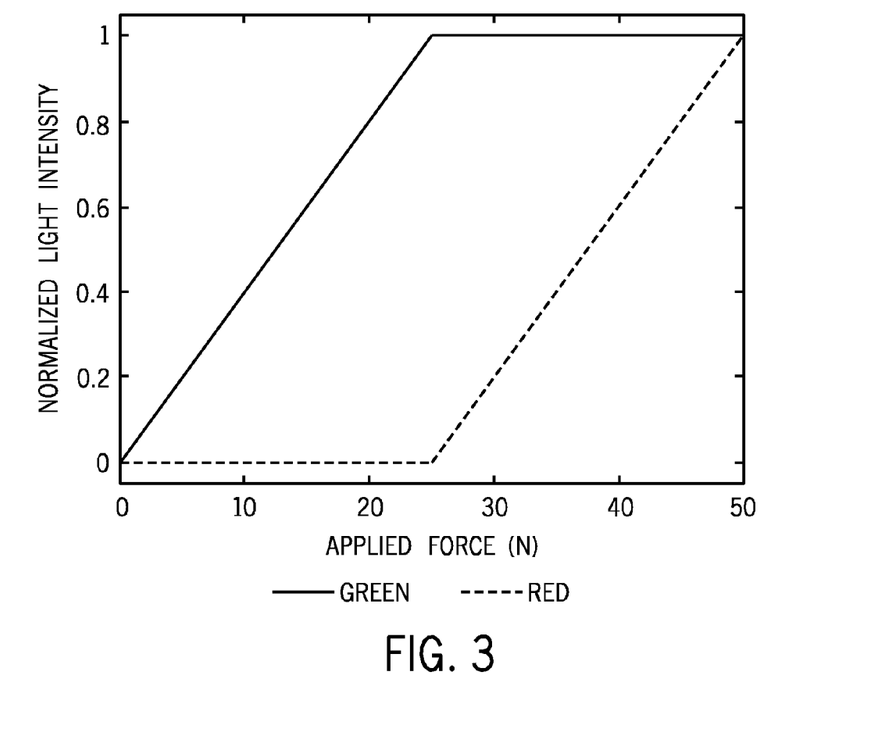
FIG. 3 is a representation of an implementation of a relationship between the measured applied grip force and the red-green light intensity.

Turning to FIG. 3, an example is presented of a relationship between the measured applied grip force and the red-green light intensity. The light intensity of each LED in an example is normalized by the maximum possible light intensity level. To help people manipulate rigid objects with a prosthesis, a LED in an example was mounted to the thumb of the Motion Control Hand to convey the applied force to the user through a change in light intensity and color. A red/green bicolor LED was used to effectively double the resolution of the visual feedback. The color scheme in an example may be fairly intuitive such as by similarity to traffic lights. Increasing green light may be used to indicate small levels of grip force. When the applied grip force exceeds a first level such as 25 N (Newtons), the red light turns on and begins to increase in intensity. The visual feedback has two frequency components, only green when the grip force is below 25 N, and fully saturated green superposed with red when the grip force is larger than 25 N.

FIG. 3 presents an example of an implementation of visually supplied force feedback. The activation points for the red and green LEDs, or any number of LEDs, may be controlled with a device in the control of the user. The user may change the level of force needed to begin activation of any LED in the device by changing the offset of the voltage representing the force sensor input to the LED, for example, with a potentiometer. The sensitivity of each LED, or any number of LEDs, relative to the measured force applied upon the environment by the manipulator may be changed, for example, with a potentiometer. The user may control whether or not two or more LEDs were active at one time and/or the amount of force that each LED needs to activate relative to one another. For example, the user may choose to turn the green LED off once the red LED becomes active. In another example, the user may have the green LED remain active for a short time and overlap the red LED until another force threshold were surpassed, at which time the green LED would turn off and only the red LED would remain active. In a further example, the user may choose to have no LED active until a predetermined level of force was applied upon the environment of the user by the manipulator. This may allow the user to calibrate the level of force to apply upon the environment ahead of time.

An example of a mathematical relationship for the bicolor LED output ($LED_O$) as a function of intensity and wavelength is $$LED_O \alpha K_G sat(F_N)\tilde{G}+f(F_N)K_R(F_N-25)\tilde{R}, \quad (5)$$

$K_G$ and $K_R$ are constant gains for the green and red lights, respectively (with units of V/N). $\tilde{G}$ and $\tilde{R}$ indicate components of light of wavelength 550 nm (green) and 500 nm (red), respectively. The $sat(F_N)$ function is defined to be $$0 \rightarrow F_N \leq 0$$

$$F_N \rightarrow 0 < F_N \leq 25 \text{ N}$$

$$25 \text{ N} \rightarrow F_N > 25 \text{ N}.$$

The function $f(F_N)$ is defined to be either zero or one when $F_N$ is less than or greater than 25 N, respectively. FIG. 3 presents an example of a graphical demonstration of equation (5).

Figure 4:
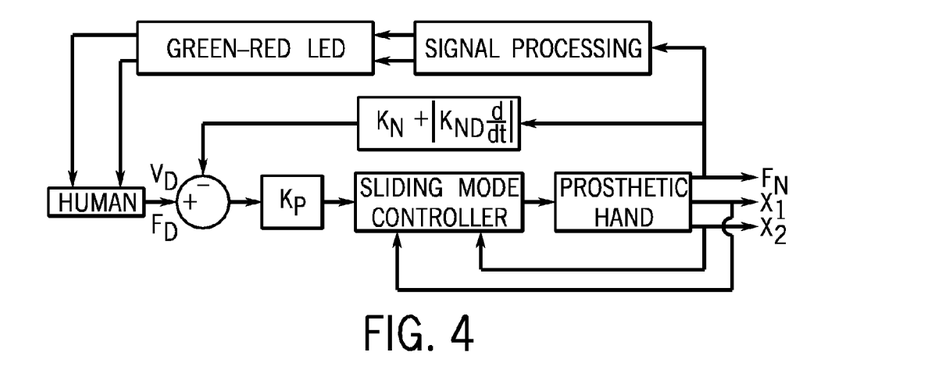
FIG. 4 is a representation of an implementation of a hybrid force-velocity sliding mode controller with first enhanced visual force feedback in which a manipulator such as a prosthetic hand is employable by a user.
Figure 5:
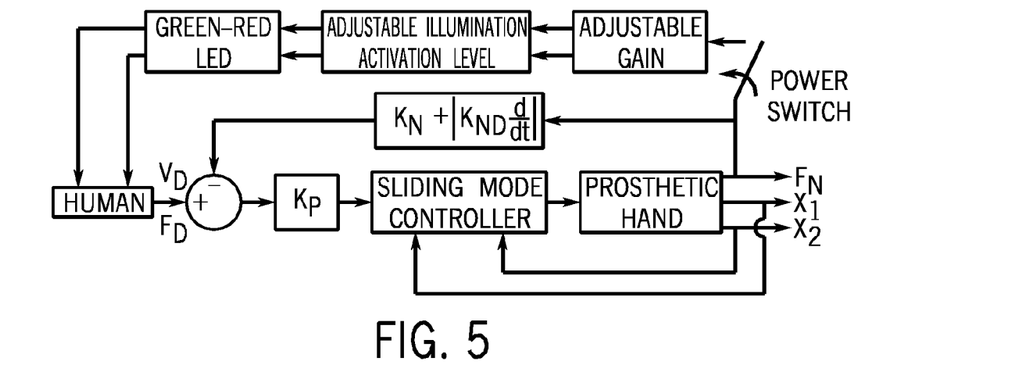
FIG. 5 is a representation of an implementation of a hybrid force-velocity sliding mode controller with second enhanced visual force feedback in which a manipulator such as a prosthetic hand is employable by a user.

Turning to FIGS. 4 and 5, examples are presented of a hybrid force-velocity sliding mode controller with enhanced visual force feedback. The enhanced visual feedback may be used in conjunction with the hybrid force-velocity sliding mode controller. An implementation of equation (5) was done analog, for example, with only several op-amps and voltage dividers. The saturation of the colors is an inherent nonlinear aspect of the light emitting diodes.

In an example of an implementation of an apparatus of FIG. 4, a manipulator such as a prosthetic hand is employed by a user. A force sensor Fn determines a force signal from a force applied by the manipulator on a part of an environment of the user. A signal modulator comprises signal processing. A visual indicator comprises a green LED and a red LED. The signal modulator is adjustable by the user to select a switch point such as 25 N in FIG. 3 for the visual indicator based on relative fragility of the part of the environment. The signal modulator employs the force signal and the switch point to control the visual indicator for the user.

Experiments were performed. The sliding mode controller was implemented in MATLAB/Simulink (The MathWorks, Natick, Mass.) with a control loop sampling frequency of 1 kHz. Myolab II (Motion Control, Inc.) was used to amplify and rectify the EMG signals of six nonamputee test subjects. EMG signals were also digitally sampled at 1 kHz and filtered online in Simulink with a first order time constant of 100 ms. Most of the EMG signal amplification is done at the site by dual channel EMG preamplifiers. One dual-site preamplifier was placed over the flexor carpi radialis muscle and another was placed over the extensor digitorum communis muscle to create a dual polarity motor command signal for the prosthesis. All six of the test subjects chose to have flexion close the prosthetic hand and extension open the prosthesis.

The six test subjects (1 female, five male) are 20-35 years of age. To quantify the usefulness of additional visual feedback, six nonamputee test subjects were asked to manipulate a rigid mechanical "egg." Another test of the bicolor LED feedback is presented because one of the six test subjects is strongly red-green color blind. An experimental prosthetic apparatus was used by the test subjects. The mechanical "egg" is similar to a real egg because no visual deflection of the "egg" is perceptible before it breaks. This type of object manipulation can pose a difficult challenge for human operators because the amount of grip force actually applied by the prosthesis is typically unknown to the user. The mass of the "egg" was made to be 1.235 kg; the force required to break the "egg" was set to be 28.7 N. This combination of "egg" mass and break force was chosen to create a moderately challenging range of possible grip forces that can be applied to successfully lift, without breaking, the "egg."

All six of the test subjects were first asked to lift and break the mechanical "egg" with their natural hands to gain a feel for the "egg." Then, the test subjects were given several minutes to become comfortable with sliding mode control (FIG. 2) of the Motion Control Hand. However, five of the six test subjects have previous experience with myoelectrically controlled prostheses because they had participated in one or more of additional research efforts. Test subjects were also given time to practice lifting the "egg" with the prosthesis using the additional visual feedback (FIG. 4) and to learn the relationship between the applied grip force and the LED output described by equation (5). The test subjects were then asked to lift, without breaking or dropping, the mechanical "egg" 15 times with the enhanced visual feedback sliding mode controller (FIG. 4). The LED was then removed from the prosthesis, and the test subjects were asked to attempt the same "egg" manipulation feat with the sliding mode controller (FIG. 2). The number of successes and failures with each controller were recorded. Finally, test subjects were asked to subjectively evaluate each control technique. The sliding mode controller (FIG. 2) was defined to be a 5 on a scale of 1 to 10. Test subjects were then asked to rate the enhanced visual feedback sliding mode controller (FIG. 4) on the same scale of 1 to 10 relative to the 5 assigned to the sliding mode controller (FIG. 2). Three weeks after the red-green color blind test subject evaluated the two controllers, he was given a 30 minute supplemental training session with the enhanced visual feedback controller. Ten days after the supplemental training session, the red-green color blind test subject repeated the experimental procedure and evaluation of the controllers of FIGS. 2 and 4.

The relative significance of the human experimental results is analyzed in MATLAB. The anova2 function is used to perform a two-way analysis of variance (ANOVA) on the "egg" break results obtained with and without additional visual feedback. The two-way ANOVA test indicates whether the differences between the controllers (FIG. 2, FIG. 4) and the six test subjects are statistically different. The ranksum function is used to perform a two-tailed nonparametric Mann-Whitney U-test on the subjective evaluations given by the test subjects. The ranksum and anova2 functions calculate p-values to indicate whether or not the additional visual feedback is statistically significant.

The individual results of each test subject are shown in Table 1. The red-green color blind person is test subject 5. Note that he subjectively rates both controllers (FIGS. 2 and 4) as a 5 on a scale of 1 to 10, even though his success rate is much better with additional visual feedback than without. Nevertheless, the nonparametric U-test shows a statistically significant difference between the subjective evaluations of the six nonamputee test subjects ($p<0.05$). The two-way ANOVA test (Table 2) shows a statistically significant difference between the performances of the test subjects ($p<0.05$). The ANOVA test also shows a significant difference in the "egg" break success rates obtained with and without additional visual feedback ($p<0.05$). These results become clearer when the overall "egg" break and subjective results from Table 1 are averaged (Table 3). The average "egg" break success rate is much higher with additional visual feedback; however, test subjects 2 and 4 have little or no improvement with the LED mounted to the thumb of the prosthesis. But, test subjects 2 and 4 both subjectively rated the enhanced visual feedback controller (FIG. 4) much higher than the sliding mode controller (FIG. 2). This is in stark contrast to the color blind test subject 5, who performs much better with the enhanced visual feedback controller (FIG. 4), but subjectively rated both controllers the same.

TABLE 1

Success rates and subjective evaluations from each individual test subject with and without additional visual feedback.

| Test Subject | 1 | 2 | 3 | 4 | 5 | 6 |
|---|---|---|---|---|---|---|
| "Egg" Break Results From 6 Nonamputee Test Subjects | | | | | | |
| LED Feedback | 11/15 | 4/15 | 5/15 | 4/15 | 9/15 | 12/15 |
| No LED Feedback | 5/15 | 4/15 | 3/15 | 3/15 | 4/15 | 9/15 |
| Subjective Evaluations From 6 Test Subjects | | | | | | |
| LED Feedback | 9 | 8 | 6 | 7.5 | 5 | 8 |
| No LED Feedback | 5 | 5 | 5 | 5 | 5 | 5 |

Test subjects used the prosthesis to lift the mechanical "egg" 15 times with each controller.

TABLE 2

Results from a two-way ANOVA analysis done on the number of successful "egg" manipulations done by each of the six test subjects.

| | Sum of Squares | DOF | Mean Squares | F Value | Prob > F |
|---|---|---|---|---|---|
| People | 77.417 | 5 | 15.4833 | 5.77 | 0.0386 |
| Controllers | 24.083 | 1 | 24.0833 | 8.98 | 0.0302 |
| Error | 13.417 | 5 | 2.6833 | | |
| Total | 114.917 | 11 | | | |

TABLE 3

Average and standard deviation (SD) of the quantitative and qualitative results from six test subjects.

| | Mean | SD |
|---|---|---|
| Overall Average "Egg" Break Results | | |
| LED Feedback | 7.50 | 3.62 |
| No LED Feedback | 4.67 | 2.25 |
| Overall Average Subjective Evaluations | | |
| LED Feedback | 7.25 | 1.47 |
| No LED Feedback | 5 | 0 |

TABLE 4

Results from the second experiment done with test subject 5.

| Test Subject | 5 |
|---|---|
| "Egg" Break Results | |
| LED Feedback | 12/15 |
| No LED Feedback | 6/15 |
| Subjective Evaluation | |
| LED Feedback | 7.5 |
| No LED Feedback | 5 |

To clarify these results, test subject 5 was asked to repeat the same experiment more than one month after the initial experiment (Table 4). Test subject 5 improved upon his previous performance with both controllers. However, he improved more with the enhanced visual feedback controller than the sliding mode controller (FIG. 2). His "egg" break success rate was twice as good with the LED mounted to the thumb than without additional visual feedback. This may explain why his subjective evaluation of the enhanced visual feedback controller is higher than the sliding mode controller in the second experiment.

An example of an implementation employs an inexpensive, light weight, and low power approach for supplying force feedback to people who use powered prosthetic hands. Grip force feedback may be mapped to light intensity and color through a bicolor LED mounted to the thumb of a prosthetic hand. Experimental results from nonamputees who lift a brittle mechanical "egg" show a statistically significant improvement when additional visual feedback is present. The subjective evaluations of the sliding mode controller with and without enhanced visual feedback also indicate a statistically significant improvement with the LED mounted to the thumb of the prosthesis.

One implementation may employ green light at a wavelength of 550 nm and red light at a wavelength of 500 nm. Another implementation may employ colors that are farther separated in the color spectrum, for example, red and blue. A further implementation may employ a single colored LED, for example, for color blind individuals and an array of different colored LEDs, for example, for others. Two or more different LEDs in an example may indicate grip force with an increase in the resolution of the visual feedback. Yet another implementation may employ a material that changes color based on the applied force. A durable cosmetic glove in an example may employ such a material.

An example of an implementation enhances size, power requirements, weight, cost, and comfort, with enhancement of people's ability to manipulate delicate or brittle objects with a prosthetic hand. When lifting and manipulating delicate objects, visual attention is typically needed even when using the natural hand. Incorporating a power switch for the LED may be desirable, for example, if the additional visual feedback was not desired or needed. Where the LED were undesired or withheld in daily use by amputees, the LED may serve as a useful and economic way to help amputees learn to deftly control a prosthetic hand during their initial meetings with a prosthetist.

Figure 6:
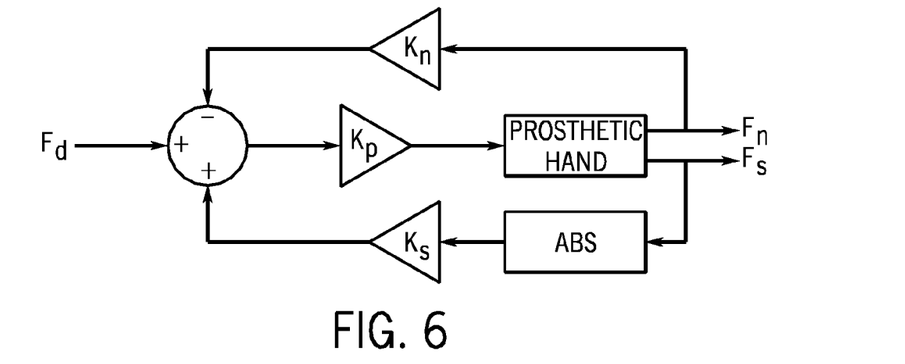
FIG. 6 is a representation of an implementation of a force controller including shear force feedback.
Figure 7:
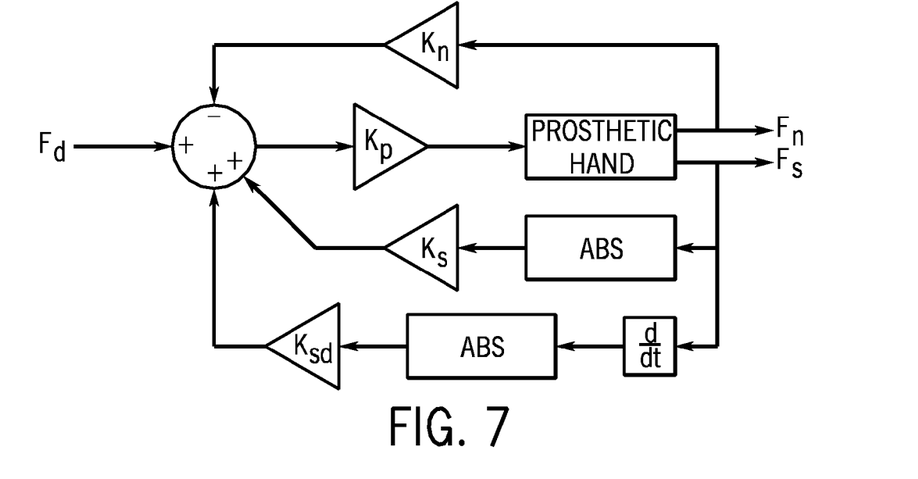
FIG. 7 is a representation of an implementation of a force controller including proportional-derivative (PD) shear force feedback.
Figure 15:
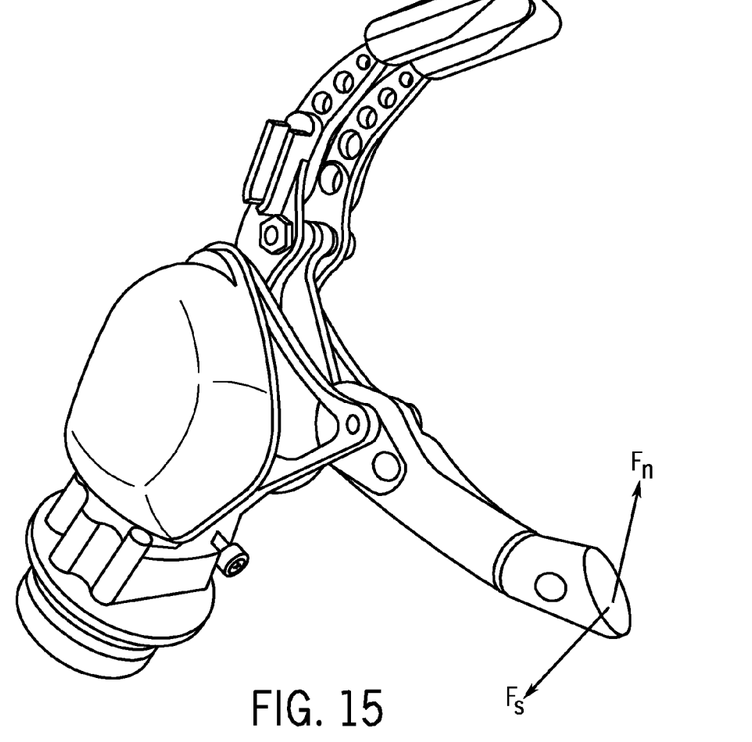
FIG. 15 is a representation of an implementation of an artificial manipulator to automatically prevent objects in grasp from slipping and falling, and illustrates an example of a direction of the shear force.

Another approach to enhance control of an artificial manipulator is to automatically prevent objects in grasp from slipping and falling. Proportional and proportional-derivative (PD) object slip prevention may be accomplished under force control by including shear force feedback or PD shear force feedback in the force controller as depicted in FIG. 6 and FIG. 7, respectively. $F_n$ is normal force for FIGS. 6, 7, 8, 15, and 16. Referring to FIG. 15, the direction of the shear force, $F_s$ in one implementation, is presented. In an example, the shear force may be applied in the direction of the normal force. In a further example, the shear force may be applied in any direction other than the normal force. Shear force feedback may be employed to compensate for steady state forces that are applied to the grasped object. Shear force derivative feedback may be employed to compensate for transient and inertial destabilizing disturbance forces applied to the grasped object. When a shear force is applied, the force error increases, which in turn tightens the grip applied by the hand proportional to the measured shear force and shear force derivative. For example, the gain for the shear force derivative may be Ksd.

The measured shear force may be applied in either the positive or negative sense, so an implementation may be arranged to feed back only the absolute value of the shear force and shear force derivative so that the hand will tighten no matter which direction the disturbance force is applied. Also, positive feedback may be employed with the shear force in contrast to the negative feedback used with the normal force. This may accommodate that an increase in normal force should decrease the input to the motor, whereas an increase in shear force should increase the input to the motor.

Figure 8:
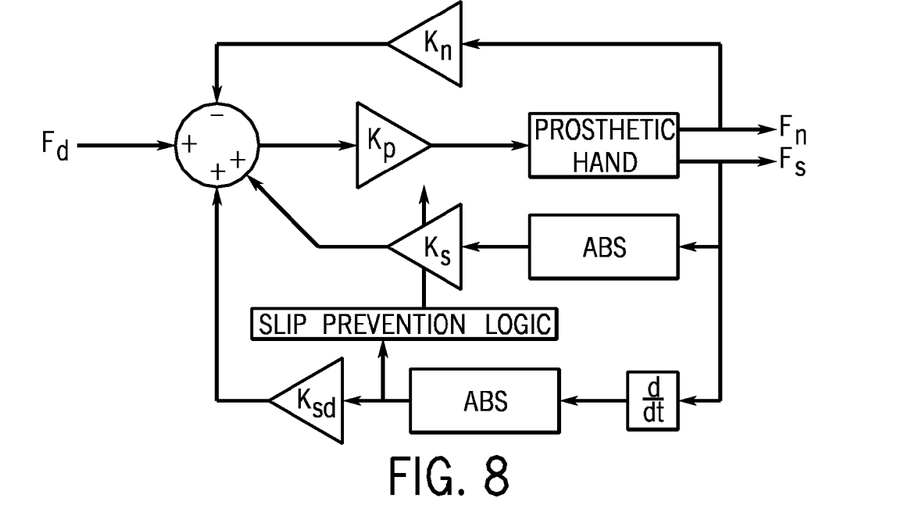
FIG. 8 is a representation of an implementation of a control scheme for adaptive object slip prevention.
Figure 9:
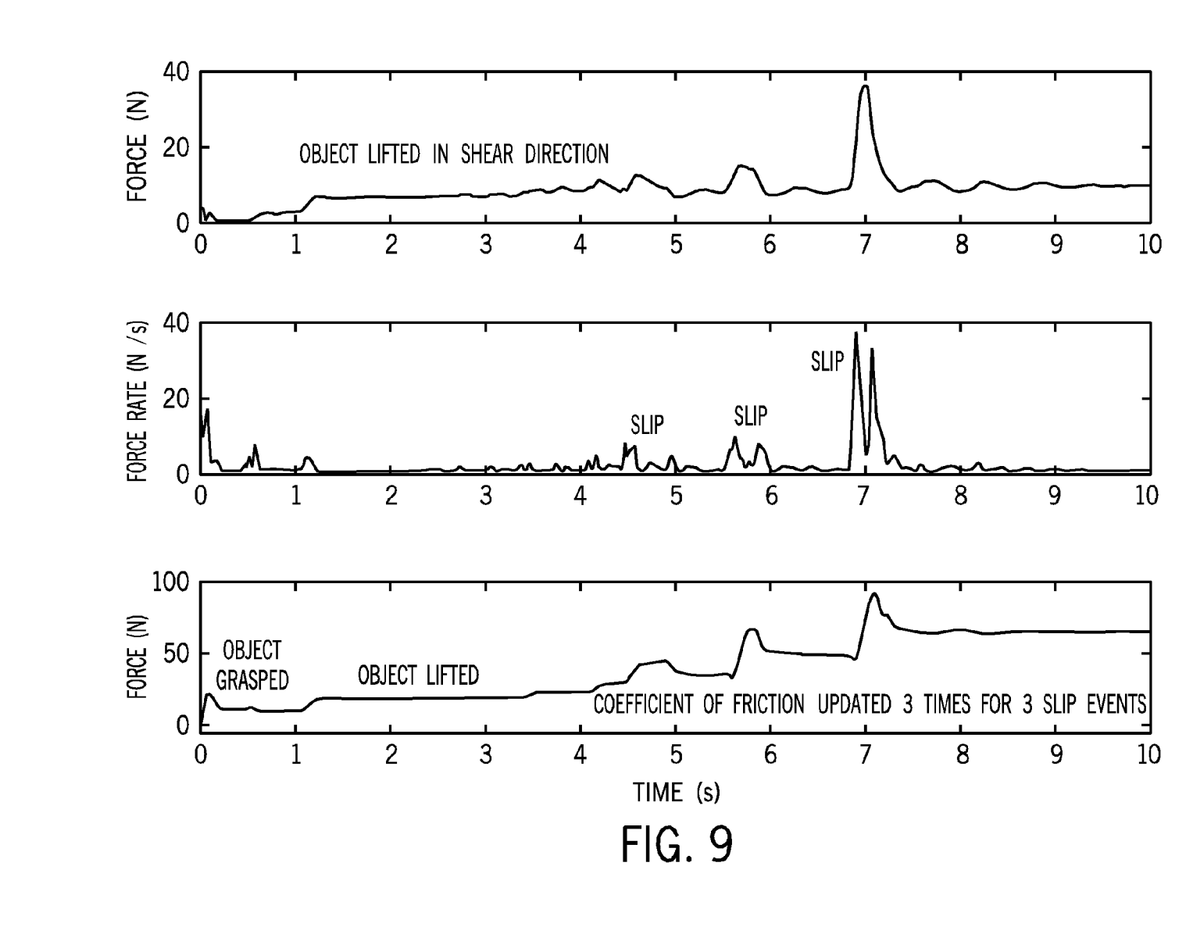
FIG. 9 is an example of a plot of an implementation of an algorithm that is employable for adaptive object slip prevention in the control scheme of FIG. 8 and represents normal force applied (bottom), shear force derivative (middle), and shear force (top) as an object is grasped, lifted, and made to slip three times by a disturbance force applied in the shear direction.

Adaptive object slip prevention may be implemented through the control scheme shown in FIG. 8. The adaption logic in an example increases the proportional shear force feedback gain, $K_s$, when slip occurs. $K_s$ may be analogous to the controller's estimate on the inverse of the coefficient of friction ($\mu$). When slip occurs, the controller's estimate of $\mu$ is decreased. The new estimate of $\mu$ is remembered and used by the controller until a larger slip event is detected or the hand is opened by the user. This algorithm is depicted by FIG. 9, which shows the normal force, shear force, and shear force derivative as an object is grasped, lifted, and made to slip three times by a disturbance force applied in the shear direction. As the object is initially lifted, the PD shear force feedback increases the applied grip force. Then, when slip occurs, the slip prevention logic based on the filtered shear force derivative increases and the shear force feedback gain, $K_s$. The amount of steady state grip force compensation then remains at a higher level so that future unwanted object slip events will be less likely to occur.

Figure 10:
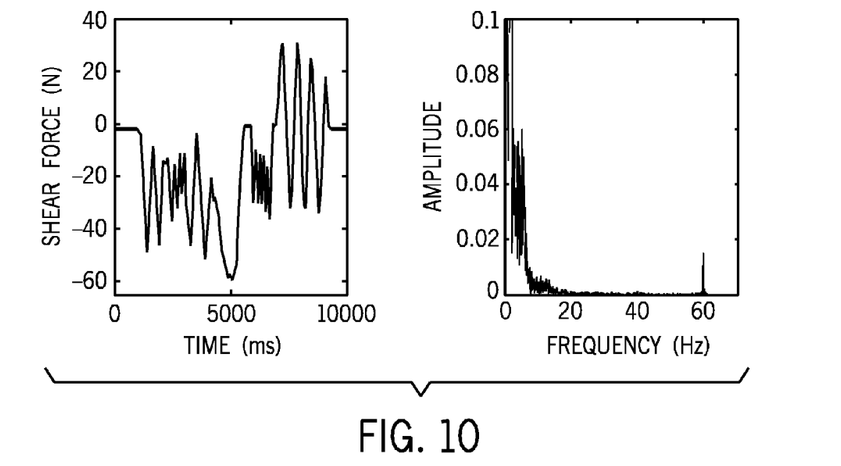
FIG. 10 is an example of a plot of shear force versus time (left) and the fast Fourier transform (FFT; right) amplitude versus frequency for nonslip events in which an object is grasped.
Figure 11:
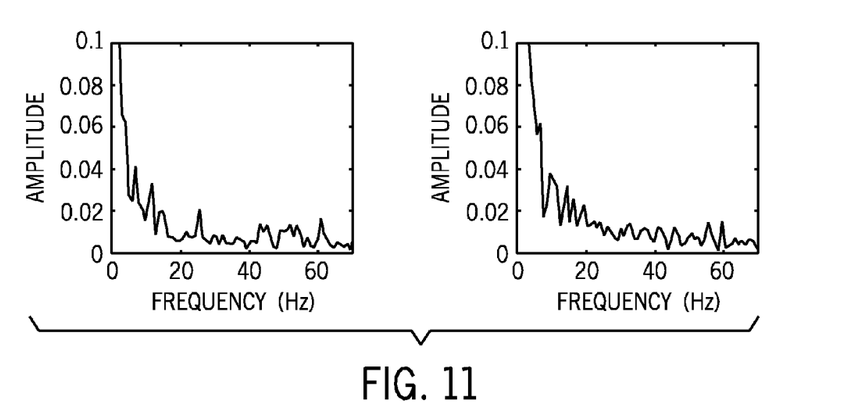
FIG. 11 is an example of a plot of the fast Fourier transform (FFT) amplitude versus frequency for rough slip (left) and smooth slip (right) events in which an object is grasped.

Force sensors equipped on the prosthesis may be employed to distinguish between slip and nonslip events. High frequency vibrations that occur during slip may be amplified by high pass or bandpass filtering the measured shear force derivative. A fast Fourier transform (FFT) examination of slip and nonslip events may show the feasibility of this idea. In FIG. 10, a very rough object is grasped with the fingertips of a commercially available cosmetic glove covering the fingers and thumb of the prosthesis. For ten seconds, the grasped object is disturbed, but not made to slip. Note the presence of high amplitude, low frequency signal components and the absence of high frequency signal components (except for the 60 Hz signal from AC electrical noise). Now, FIG. 11 shows the FFT of individual slip events that occur while grasping a very smooth object ($\mu=0.54$) and a very rough object ($\mu=0.81$). Note the widespread presence of high frequency vibrations which are present between 25 Hz and 60 Hz. These vibrations are amplified to detect when a grasped object slips.

One of the bandpass filters of the measured shear force used in these experiments to detect slip is $$s\left[\frac{250^2}{s^2+12.5s+250^2}\right]\left[\frac{345}{s+345}\right]$$

This third order transfer function is designed to provide several performance attributes. First, it differentiates the shear force so that high amplitude, low frequency (steady state) signals will not be mistaken as slip. A second order transfer function is then designed to resonate near 40 Hz. Finally, a low pass filter with a cutoff frequency near 55 Hz is implemented to attenuate 60 Hz noise.

Figure 12:
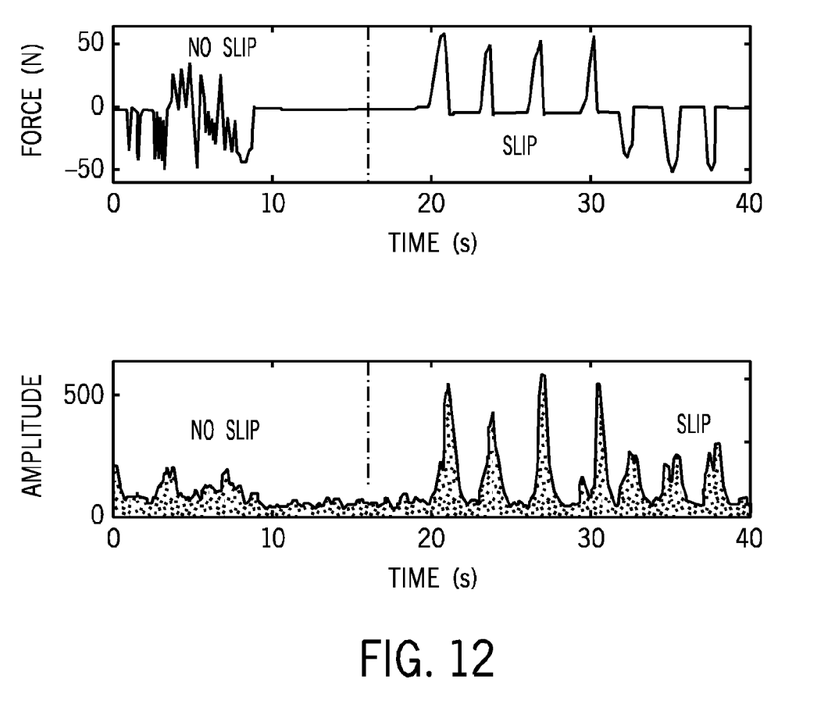
FIG. 12 is a representation of an approach to slip detection in which an object is grasped, disturbed, not made to slip, and then made to slip seven times with an example of a plot of measured shear force (top) versus time and the superposition of seven, third order bandpass filters (bottom) amplitude versus time.

Referring to FIG. 12, an example of an approach to slip detection is presented. For example, the measured shear force is shown over a 40 second duration of time. In the first 10 seconds, the same smooth object ($\mu=0.54$) is grasped, disturbed, but not made to slip. Then, in the second half of the experiment, the grasped object is made to slip seven times. In the bottom of FIG. 12 is the superposition of seven bandpass filters of the same form as listed above. The difference is that the natural frequencies of the seven bandpass filters are set to resonate at 25 Hz, 30 Hz, 35 Hz, and so on up to 55 Hz. Simultaneously monitoring multiple filters in an example serves to accommodate different slip events having different frequency components between 25 Hz and 55 Hz present in the measured shear force (FIG. 11). Each of the seven bandpass filters performs differently because they each amplify a different frequency band of the measured shear force derivative. Based on frictional conditions of the grasped object, surface texture, and speed of slip, one bandpass filter in an example will be a better indicator of slip than the other bandpass filters. Notice that the slip events are distinguishable from the nonslip events even through the thick cosmetic glove (FIG. 12).

An example of an approach for object slip detection has been presented, among a variety of possible approaches to determine if an object slips. Another approach may involve a sensor, for example, specialized sensors such as for the purpose of determining if an object is slipping from a stable grasp. A further approach may employ video cameras or other optical techniques to ascertain if object slip is occurring. For a wide variety of approaches used to determine if an object slips from a stable grasp, the control algorithm illustrated by FIG. 8 and FIG. 9 in an example may be used to compensate for any perceived object slip. Regardless of the source of slip detection, an example of the approach of visual feedback from an LED or plurality of LEDs may also be used to inform the user if an object slips from the manipulator. This enables the user, even when not observing the manipulator, to compensate the applied grip force on the environment to prevent the object from falling.

Another method of automatically preventing any grasped object from slipping from an artificial manipulator is to increase the applied grip force relative to the measured acceleration of any other degrees of freedom within the manipulator. Thus, in this example, grip force, grip force derivative, and wrist acceleration feedback are included in the controller for the end effector of the manipulator, FIG. 13.

Figure 13:
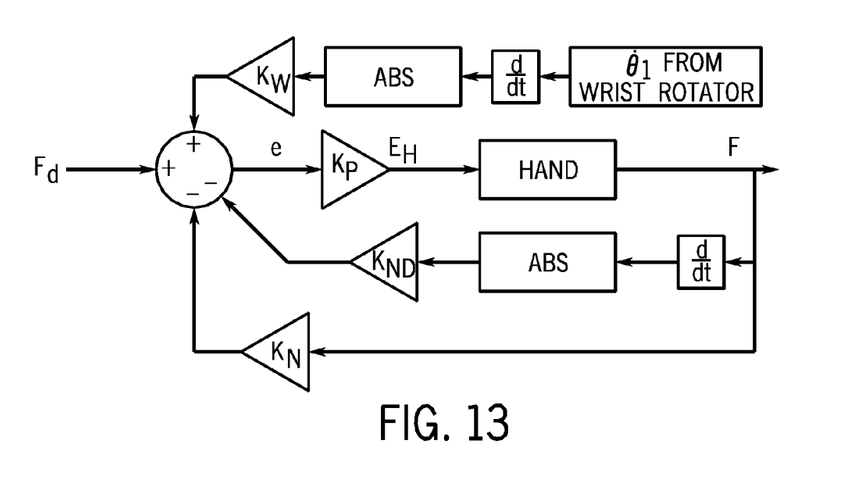
FIG. 13 is a representation of an implementation of a controller for an end effector of a manipulator, illustrating the controller with grip force, grip force derivative, and wrist acceleration feedback.
Figure 14:
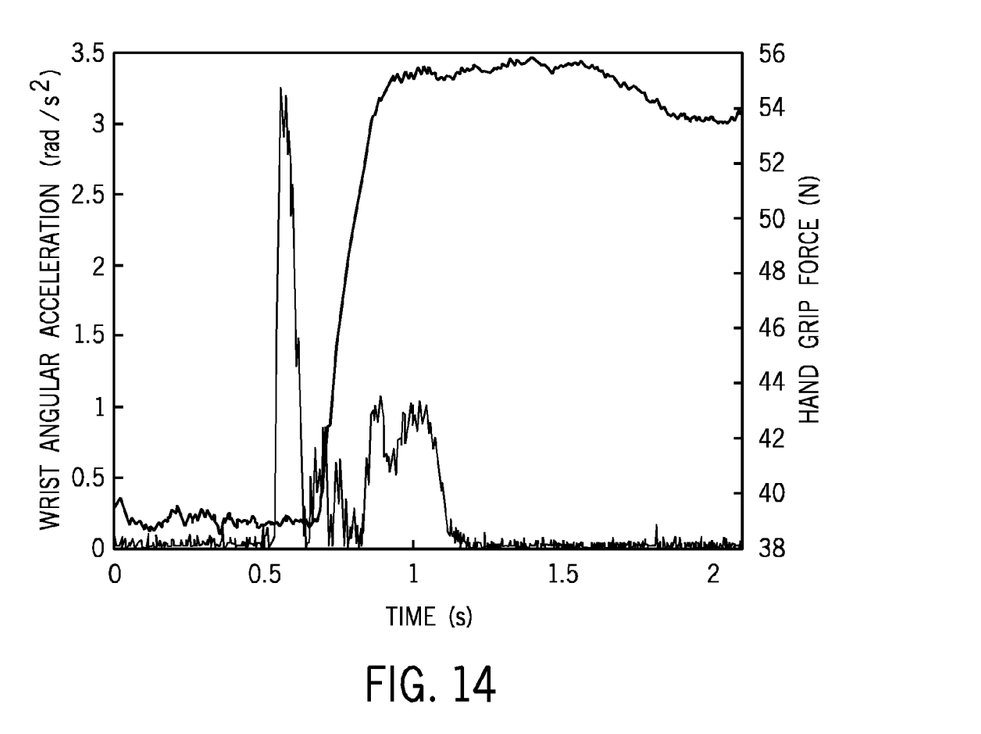
FIG. 14 is an example of a plot of an implementation of a controller such that when the angular acceleration of the wrist increases, the applied grip force of the end effector of the manipulator is automatically increased to prevent the grasped object from slipping.

The control law is $$E_H = K_P\left(F_d + K_W\left|\frac{d\dot{\theta}_1}{dt}\right| - K_{ND}\left|\frac{dF}{dt}\right| - K_N F\right)$$

where $E_H$ is the voltage input to the hand, $F_d$ is the desired grip force, $\dot{\theta}_1$ is the measured wrist angular velocity, and F is the measured grip force. $F_d$, is the desired force supplied by the user. The K terms are proportional constants used to weight each component. An example of how this controller works is shown in FIG. 14. When the angular acceleration of the wrist increases, the applied grip force of the end effector of the manipulator is automatically increased to prevent the grasped object from slipping.

The apparatus may comprise an exemplary implementation of an algorithm, procedure, program, process, mechanism, sensor, engine, model, coordinator, module, application, software, code, and/or logic.

An implementation of the apparatus comprises a plurality of components such as one or more of electronic components, chemical components, organic components, mechanical components, hardware components, optical components, and/or computer software components. A number of such components can be combined or divided in an implementation of the apparatus. In one or more exemplary implementations, one or more features described herein in connection with one or more components and/or one or more parts thereof are applicable and/or extendible analogously to one or more other instances of the particular component and/or other components in the apparatus. In one or more exemplary implementations, one or more features described herein in connection with one or more components and/or one or more parts thereof may be omitted from or modified in one or more other instances of the particular component and/or other components in the apparatus. An exemplary technical effect is one or more exemplary and/or desirable functions, approaches, and/or procedures. An implementation of the apparatus comprises any (e.g., horizontal, oblique, angled, or vertical) orientation, with the description and figures herein illustrating an exemplary orientation of an exemplary implementation of the apparatus, for explanatory purposes.

An implementation of the apparatus encompasses an article and/or an article of manufacture. The article comprises one or more computer-readable signal-bearing media. The article comprises means and/or instructions in the one or more media for one or more exemplary and/or desirable functions, approaches, and/or procedures.

An implementation of the apparatus employs one or more computer readable signal bearing media. A computer-readable signal-bearing medium stores software, firmware and/or assembly language for performing one or more portions of one or more implementations. An example of a computer-readable signal bearing medium for an implementation of the apparatus comprises a memory and/or recordable data storage medium. A computer-readable signal-bearing medium for an implementation of the apparatus in an example comprises one or more of a magnetic, electrical, optical, biological, chemical, and/or atomic data storage medium. For example, an implementation of the computer-readable signal-bearing medium comprises one or more floppy disks, magnetic tapes, CDs, DVDs, hard disk drives, and/or electronic memory. In another example, an implementation of the computer-readable signal-bearing medium comprises a modulated carrier signal transmitted over a network comprising or coupled with an implementation of the apparatus, for instance, one or more of a telephone network, a local area network (LAN), a wide area network (WAN), the Internet, and/or a wireless network. A computer-readable signal-bearing medium in an example comprises a physical computer medium and/or computer-readable signal-bearing tangible medium.

The steps or operations described herein are examples. There may be variations to these steps or operations without departing from the spirit of the invention. For example, the steps may be performed in a differing order, or steps may be added, deleted, or modified.

Although exemplary implementation of the invention has been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
   a manipulator operable by a user;
   a force sensor that determines a force signal from a force applied by the manipulator on a part of an environment of the user;
   a signal modulator; a visual indicator;
   wherein the signal modulator is adjustable by the user to select a switch point for the visual indicator based on relative fragility of the part of the environment;
   wherein the signal modulator employs the force signal and the switch point to control the visual indicator for the user;
   wherein light intensity of the visual indicator is related to a magnitude of the force applied by the manipulator; and wherein the visual indicator comprises at least one LED including a first LED and a second LED, wherein the signal modulator employs the force signal at a first level below the switch point to turn on the first LED, wherein the signal modulator employs the force signal at a second level above the switch point to turn on the second LED.

2. The apparatus of claim 1, wherein the manipulator comprises at least one of an active manipulator and a passive manipulator.

3. The apparatus of claim 1, wherein the manipulator comprises a prosthetic hand, a prosthetic foot, or a robotic manipulator.

4. The apparatus of claim 1, wherein the at least one LED comprises a plurality of colors.

5. The apparatus of claim 1, wherein the visual indicator comprises a plurality of colors.

6. The apparatus of claim 1, wherein the user has control of gain of the visual indicator to make the visual indicator more or less sensitive to the force applied by the manipulator on the part of the environment.

7. The apparatus of claim 1, wherein the visual indicator comprises a plurality of LEDs with light intensity gains adjustable at discretion of the user.

8. The apparatus of claim 1, further comprising one or more sensors to measure at least one of velocity and acceleration of at least one independent degree of freedom of the manipulator, wherein the force applied on the part of the environment of the user by the manipulator is performed automatically relative to the measured at least one of velocity and acceleration of the independent degree of freedom of the manipulator.

9. An apparatus, comprising:
a manipulator operable by a user, wherein the manipulator comprises at least one independent degree of freedom;
a force sensor that determines a force signal from a force applied by the manipulator on a part of an environment of the user;
wherein the force sensor is differentiated to indicate rate of change of the force applied by the manipulator on the part of the environment;
one or more sensors to measure at least one of velocity and acceleration of the at least one independent degree of freedom of the manipulator, wherein the force applied on the part of the environment of the user by the manipulator is performed automatically relative to the measured at least one of velocity and acceleration of the independent degree of freedom of the manipulator;
a signal modulator; and
a visual indicator;
wherein the signal modulator is adjustable by the user to select a switch point for the visual indicator based on relative fragility of the part of the environment;
wherein the signal modulator employs the force signal and the switch point to control the visual indicator for the user.

10. The apparatus of claim 9, wherein at least one of a measured force derivative, an absolute value of the measured force derivative, and a measured force is employed in a control algorithm to increase sensitivity of the force applied by the manipulator on the environment.

11. The apparatus of claim 9, wherein the visual indicator is activated by a sum of a measured force, Fn, and a derivative of Fn or an absolute value of a derivative of Fn, as a control input for an LED or a plurality of LEDs of the a visual indicator.

12. The apparatus of claim 9, wherein light intensity of the visual indicator is related to a magnitude of the force applied by the manipulator.

13. An apparatus, comprising:
a manipulator operable by a user; wherein the manipulator comprises at least one independent degree of freedom;
one or more sensors to measure at least one of velocity and acceleration of the at least one independent degree of freedom of the manipulator, wherein a force applied on a part of an environment of the user by the manipulator is performed automatically relative to the measured at least one of velocity and acceleration of the independent degree of freedom of the manipulator;
a force sensor to determine a force signal from the force applied by the manipulator on the part of the environment of the user;
a signal modulator; and
a visual indicator;
wherein the signal modulator is adjustable by the user to select a switch point for the visual indicator based on relative fragility of the part of the environment; and
wherein the signal modulator employs the force signal and the switch point to control the visual indicator for the user.

14. The apparatus of claim 13, wherein the visual indicator displays the measured at least one of velocity and acceleration of the at least one independent degree of freedom of the manipulator, wherein the visual indicator is employable by the user when not looking at the manipulator to inform the user of the measured at least one of velocity and acceleration of the at least one independent degree of freedom of the manipulator to adjust the force applied by the manipulator on the part of the environment.

15. The apparatus of claim 13, wherein light intensity of the visual indicator is related to a magnitude of the force applied by the manipulator.

16. An apparatus, comprising:
a manipulator operable by a user, wherein the manipulator comprises at least one independent degree of freedom;
a force sensor that determines a force signal from a force applied by the manipulator on a part of an environment of the user;
a sensor that determines if an object grasped by the manipulator is slipping from a stable grasp of the manipulator operated by the user;
one or more sensors to measure at least one of velocity and acceleration of the at least one independent degree of freedom of the manipulator, wherein the force applied on the part of the environment of the user by the manipulator is performed automatically relative to the measured at least one of velocity and acceleration of the independent degree of freedom of the manipulator;
a signal modulator; and
a visual indicator;
wherein the signal modulator is adjustable by the user to select a switch point for the visual indicator based on relative fragility of the part of the environment;
wherein the signal modulator employs the force signal and the switch point to control the visual indicator for the user.

17. The apparatus of claim 16, wherein the visual indicator becomes active when the object grasped by the manipulator slips from the stable grasp.

18. The apparatus of claim 16, wherein light intensity of the visual indicator is related to a magnitude of the force applied by the manipulator.

19. An apparatus, comprising:
a manipulator operable by a user;
a force sensor that determines a force signal from a force applied by the manipulator on a part of an environment of the user, wherein the force sensor responds to vibrations that occur during object slip;
a filter that amplifies measured vibrations by filtering a force signal derivative, wherein the filter comprises a second order transfer function;
a signal modulator; and
a visual indicator,
wherein the signal modulator is adjustable by the user to select a switch point for the visual indicator based on relative fragility of the part of the environment; and
wherein the signal modulator employs the force signal and the switch point to control the visual indicator for the user.

20. The apparatus of claim 19, wherein the force applied by the manipulator on the environment is automatically increased relative to the shear force or absolute value of the measured shear force.

21. The apparatus of claim 19, wherein the filter comprises at least one of a high-pass and a band-pass filter.

22. The apparatus of claim 19, wherein the force applied by the manipulator on the environment is automatically increased and maintained to prevent future occurrences of object slip.

23. The apparatus of claim 19, wherein the filter comprises a third order transfer function.

24. The apparatus of claim 19, further comprising one or more sensors to measure at least one of velocity and acceleration of at least one independent degree of freedom of the manipulator, wherein the force applied on the part of the environment of the user by the manipulator is performed automatically relative to the measured at least one of velocity and acceleration of the independent degree of freedom of the manipulator.

25. The apparatus of claim 19, wherein light intensity of the visual indicator is related to a magnitude of the force applied by the manipulator.

* * * * *